(12) United States Patent
Gottemoller

(10) Patent No.: US 6,677,327 B1
(45) Date of Patent: Jan. 13, 2004

(54) PHYTOSTEROL AND PHYTOSTANOL COMPOSITIONS

(75) Inventor: Thomas V. Gottemoller, Mt. Zion, IL (US)

(73) Assignee: Archer-Daniels-Midland Company, Decatur, IL (US)

(*) Notice: Subject to any disclaimer, the term of this patent is extended or adjusted under 35 U.S.C. 154(b) by 0 days.

(21) Appl. No.: 09/444,713

(22) Filed: Nov. 24, 1999

(51) Int. Cl.$^7$ ........................... A61K 31/56; A61K 9/00; A61K 38/00; A61K 47/00
(52) U.S. Cl. ................. 514/182; 424/439; 424/489; 424/499; 426/590; 426/654; 426/656; 426/657; 426/662; 514/2; 514/169; 514/170; 514/171; 514/773; 514/775; 514/785; 514/786; 514/788; 514/975
(58) Field of Search ................. 514/729, 773, 514/774, 775, 776, 777, 778, 783, 785, 786, 975, 2, 169, 170, 171, 182, 788; 424/439, 489, 499; 426/590, 654, 656, 657, 662

(56) References Cited

U.S. PATENT DOCUMENTS

| | | | |
|---|---|---|---|
| 3,004,043 A | 10/1961 | Stern | 260/397.2 |
| 3,085,939 A | 4/1963 | Wruble et al. | 167/65 |
| 3,881,005 A | 4/1975 | Thakkar et al. | 424/238 |
| 4,192,811 A | 3/1980 | Foster | 260/397.25 |
| 4,222,949 A | 9/1980 | Foster | 260/397.25 |
| 4,260,603 A | 4/1981 | Pegel et al. | 424/182 |
| 4,325,880 A | 4/1982 | Foster | 260/397.2 |
| 4,393,044 A | 7/1983 | Takada et al. | 424/59 |
| 4,420,427 A | 12/1983 | Hamunen | 260/397.25 |
| 4,428,885 A | 1/1984 | Higaki et al. | 260/410.9 |
| 4,588,717 A | 5/1986 | Mitchell | 514/170 |
| 4,604,281 A | 8/1986 | Deckner et al. | 424/59 |
| 4,705,875 A | 11/1987 | Mitchell | 556/46 |
| 5,004,737 A | 4/1991 | Kim et al. | 514/182 |
| 5,023,249 A | 6/1991 | Kondo et al. | 514/170 |
| 5,032,585 A | 7/1991 | Lichtenberger | 514/78 |
| 5,043,329 A | 8/1991 | Lichtenberger | 514/78 |
| 5,100,662 A | 3/1992 | Bolcsak et al. | 424/88 |
| 5,117,016 A | 5/1992 | Tackett et al. | 552/545 |
| 5,244,887 A | 9/1993 | Straub | 514/182 |
| 5,270,041 A | 12/1993 | Eugster et al. | 424/195.1 |
| 5,502,045 A | 3/1996 | Miettinen et al. | 514/182 |
| 5,700,396 A | 12/1997 | Suzuki et al. | 252/309 |
| 5,747,464 A | 5/1998 | See | 514/26 |
| 5,932,562 A | 8/1999 | Ostlund, Jr. | 514/78 |
| 5,958,913 A | 9/1999 | Miettenen et al. | 514/182 |
| 6,054,144 A | 4/2000 | Burruano et al. | 424/464 |
| 6,063,776 A | 5/2000 | Ostlund, Jr. | 514/182 |
| 6,087,353 A * | 7/2000 | Stewart et al. | 514/182 |
| 6,113,972 A * | 9/2000 | Corliss et al. | 426/613 |
| 6,162,483 A | 12/2000 | Wester | 426/607 |
| 6,171,638 B1 | 1/2001 | Gugger et al. | 426/634 |
| 6,190,720 B1 | 2/2001 | Yuan et al. | 426/601 |
| 6,544,566 B1 | 4/2003 | Waggle et al. | 424/757 |
| 2001/0024666 A1 | 9/2001 | Waggle et al. | 424/757 |
| 2001/0026814 A1 | 10/2001 | Waggle et al. | 525/757 |
| 2001/0029248 A1 | 10/2001 | Waggle et al. | 514/27 |
| 2002/0107232 A1 | 8/2002 | Flickinger et al. | 514/182 |
| 2003/0003131 A1 | 1/2003 | Dyer et al. | 424/439 |

FOREIGN PATENT DOCUMENTS

| | | |
|---|---|---|
| DE | 38 27 953 | 2/1990 |
| DE | 40 38 385 C2 | 6/1992 |
| EP | 0 289 636 A1 | 11/1988 |
| EP | 0 442 350 | 8/1991 |
| EP | 0 828 434 B1 | 3/1998 |
| EP | 0 839 458 A1 | 5/1998 |
| EP | 0 897 671 A1 | 2/1999 |
| EP | 0911385 A1 | 4/1999 |
| EP | 0 947 197 | 10/1999 |
| EP | 1 046 396 A2 | 10/2000 |
| GB | 931115 | 7/1963 |
| GB | 1284814 | 8/1972 |
| GB | 1405346 | 9/1975 |
| JP | 03076557 A * | 4/1991 |
| JP | 9135672 | 5/1997 |
| WO | WO 95/08342 | 3/1995 |
| WO | WO 96/38047 | 12/1996 |
| WO | WO 98/06405 | 2/1998 |
| WO | WO 98/23275 | 6/1998 |
| WO | WO 98/23277 | 6/1998 |
| WO | WO 98/57545 | 12/1998 |
| WO | WO 98/58554 | 12/1998 |
| WO | WO 99/25362 | 5/1999 |
| WO | WO 99/30569 | 6/1999 |
| WO | WO 99/39715 | 8/1999 |
| WO | WO 99/39715 | 9/1999 |
| WO | WO 99/43218 | 9/1999 |
| WO | WO 99/48378 | 9/1999 |
| WO | WO 99/53925 | 10/1999 |
| WO | WO 99/56729 A1 | 11/1999 |
| WO | WO 00/52029 A1 | 9/2000 |
| WO | WO 00/61694 A1 | 10/2000 |
| WO | WO 02/28204 A1 | 4/2002 |

OTHER PUBLICATIONS

West online, file Derwent, Acc. No. 1991–137940, JP 03076557 A (1991), Abstract.*

STN/CAS online, file Caplus, Acc. No. 1991:534651, Doc. No. 115:134651, JP 03076557 (1991), Abstract.*

(List continued on next page.)

*Primary Examiner*—S. Mark Clardy
*Assistant Examiner*—Frank Choi
(74) *Attorney, Agent, or Firm*—Sterne, Kessler, Goldstein & Fox P.L.L.C.

(57) ABSTRACT

The present invention relates to an edible phytosterol or phytostanol composition useful in the food industry and to methods of preparing such an edible composition. The edible composition comprises a phytosterol or phytostanol, an isolated water soluble protein, and optionally an emulsifier, wherein the weight ratio of the protein to the phytosterol or phytostanol is from about 0.2:1 to about 10:1, and the weight ratio of the emulsifier to the phytosterol or phytostanol is from about 0.2:1 to about 5:1. The invention also relates to edible products containing such a composition and to methods for the production of the edible products.

19 Claims, No Drawings

OTHER PUBLICATIONS

Lanzani, A. et al., "Minor lipidic constituents typical of certain seed meals and of their proteic derivatives," *La Rivista Italiana Delle Sostanze Grasse 54*:448–450 (1977).

Tanaka, T., "Antibacterial Preparation and Antimycotic Preparation," *Patent Abstracts of Japan 1995* (1995).

Dialog File 351, Accession No. 1989–305476, Derwent WPI English language abstract for JP 01 226812 A.

Dialog File 351, Accession No. 1997–335979/199731, Derwent WPI English language abstract for JP 9135672 A.

Dialog File 351, Accession No. 1992–193100/199224, Derwent WPI English language abstract for DE 40 38 385 C2.

Partial International Search Report for International Application No. PCT/US00/01641, mailed Jul. 26, 2000.

Kramer, J.K.G. and Hulan, H.W., "Artifacts produced during acid–catalyzed methanolysis of sterol esters," *J. Lipid Res.* 17:674–676, Lipid Research, Inc. (1976).

Gylling, H., and Miettinen, T.A., "Serum cholesterol and cholesterol and lipoprotein metabolism in hypercholesterolaemic NIDDM patients before and during sitostanol ester––margarine treatment," *Diabetologia 37*:773–780. (1994).

Miettinen, T.A., and Vanhanen, H., "Dietary sitostanol related to absorption, synthesis and serum level of cholestrol in different apolipoprotein E phenotypes," *Atherosclerosis 105*:217–226 (1994).

Miettinen, T.A., et al., "Reduction of Serum Cholesterol with Sitostanol–ester Margarine in a Mildly Hypercholesterolemic Population," *New England J. Med. 333*:1308–1312 (1995).

Vanhanen, H.T., et al., "Serum cholesterol, cholesterol precursors, and plant sterols in hypercholesterolemic subjects with different apoE phenotypes during dietary sitostanol ester treatment," *J. Lipid Res. 34*:1535–1544 (1993).

Vanhanen, H.T., et al., "Serum levels, absorption efficiency, faecal elimination and synethesis of cholesterol during increasing doses of dietary sitostanol esters in hypercholesterolaemic subjects," *Clin. Sci. 87*:61–67 (1994).

English language abstract of JP 07–118169, Patent Abstracts of Japan.

English language abstract of DE 38 27 953, Document No. AN5, Derwent World Patents Index Accession No. 1990–059813.

English language abstract of EP 0 442 350, Document No. AO5, Derwent World Patents Index Accession No. 1991–247073.

International Search Report for International Application No. PCT/US00/01641, mailed Oct. 13, 2000.

Vohra, P., et al., "Fractionation of Soybean Oil Meal for Growth and Antiperotic Factors," *Poultry Science 38*:1476–1477, Poultry Science Association (1959).

* cited by examiner

PHYTOSTEROL AND PHYTOSTANOL COMPOSITIONS

BACKGROUND OF THE INVENTION

1. Field of the Invention

The present invention relates to an edible phytosterol or phytostanol composition useful in the food industry and a method of preparing such an edible composition. The invention also relates to edible products containing such a composition and to methods for the production of the edible products.

2. Related Art

Phytosterols are plant sterols structurally similar to cholesterol that have been known for many years to reduce cholesterol absorption and serum cholesterol levels while not being absorbed themselves. Chemically, natural sterols are $C_{26}$–$C_{30}$ steroid alcohols which have an aliphatic side chain at the $C_{17}$ position. The differences between a cholesterol molecule and a phytosterol molecule are primarily found in the structure of the side chain of the basic frame. Plant sterols may also be hydrogenated to produce plant stanols, i.e., phytostanols.

Since phytosterols are natural components of vegetable fats and oils which are non-toxic and inexpensive byproducts of food processing, they may be important in the treatment of individuals with mildly-increased serum cholesterol, or for the general population in food products or dietary supplements. However, the use of phytosterols has not been very extensive primarily due to their poor solubility; they are poorly soluble in fats and insoluble in water. Therefore, the production of edible products containing phytosterols is technically difficult, and the final products are often not organoleptically pleasing in structure and mouthfeel.

Several investigators have proposed ways to increase the solubility or bioavailability of phytosterols in order to make them more useful. For example, attempts have been made to increase the solubility of phytosterols by producing fat-soluble forms, such as fatty acid esters, by dissolving or emulsifying the phytosterols or their derivatives in a fat or fat component or by other esterification procedures. Methods of preparing fat-soluble phytosterol esters are disclosed, for example, in U.S. Pat. No. 5,502,045.

In addition, solubilized sterol compositions are disclosed, for example, in EP 839 458 and in U.S. Pat. No. 5,244,887. EP 839 458 describes oilsolubilized solutions consisting of sitosterol-containing phytosterols, vitamin E and emulsifiers which can be added to foods. U.S. Pat. No. 5,244,887 describes the use of stanols, phytosterol derivatives in which all carbon-carbon bonds in the rings are saturated, as food additives to reduce cholesterol absorption from foods and beverages which contain cholesterol. The disclosed method comprises the step of dissolving a stanol selected from the group consisting of clionastanol, 22,23 dihydrobrassicastanol, campestanol, sitostanol and mixtures thereof, with an edible solubilizing agent such as triglyceride, an effective amount of a suitable antioxidant such as tocopherol and an effective amount of a suitable dispersant such as lecithin.

Phytosterol compositions which do not contain triglycerides or oils have also been disclosed. International Publication No. WO 98/58554 describes a premix useful in the food industry, particularly in bakery products. The disclosed premix contains a pulverized plant sterol and/or stanol and a conventional foodstuff raw material that is selected from a group comprising cereal, leguminous plants, milk powder, fruits, vegetables and/or berries, fish, meat, bone, feather and rind, and has a mean particle size of less than about 600 µm.

U.S. Pat. No. 5,932,562 describes compositions and methods useful for reducing cholesterol absorption from the intestine. The disclosed phytosterol composition is in solid, but water soluble form, and comprises an aqueous homogeneous micellar mix of a plant sterol and lecithin which has been dried to a finely divided water soluble powder, wherein the mole ratio of said plant sterol to lecithin is within the range of 1:1 to 1:10.

Currently, physical mixtures of phytosterols and food products and/or ingredients do not produce a smooth product without chemical modification of the phytosterols. As such, there is a need in the art for edible products containing phytosterols and/or phytostanols which do not require the use of triglycerides or oils as a carrier, can be effectively incorporated into a variety of edible consumer products regardless of cholesterol or fat content and remain homogeneously dispersed, are convenient and cost-effective to produce, are stable in storage, and contain a smooth and pleasing mouthfeel.

SUMMARY OF THE INVENTION

It is therefore an object of the present invention to provide an edible phytosterol or phytostanol composition which can be utilized as such as a functional food or incorporated in aqueous or powder form into foods and beverages with improved stability and without chemical modification, and which imparts a smooth and pleasing mouthfeel. Other objects, features and advantages of the present invention will be set forth in the detailed description of preferred embodiments that follows, and in part will be apparent from the description or can be learned by practice of the invention. These objects and advantages of the invention will be realized and attained by the compositions and methods particularly pointed out in the written description and claims hereof.

These and other objects are accomplished by the compositions and methods of the present invention, which, in a first embodiment, are broadly directed to an aqueous edible composition comprising a phytosterol or phytostanol and an isolated water soluble protein, wherein the weight ratio of the protein to the phytosterol or phytostanol is from about 0.2:1 to about 10:1. Other aspects and embodiments of the present invention will be described in more detail below.

It is to be understood that both the foregoing general description and the following detailed description are exemplary and explanatory only and are intended to provide further explanation of the invention as claimed.

DETAILED DESCRIPTION OF THE PREFERRED EMBODIMENTS

In one aspect of the invention there is provided a non-soluble, water dispersible aqueous edible composition comprising a phytosterol and an isolated water soluble protein, wherein the weight ratio of the protein to the phytosterol or phytostanol is from about 0.2:1 to about 10:1.

As used herein, the term "phytosterol" includes all phytosterols, for example, sitosterol, campesterol, stigmasterol, taraxasterol, and any derivatives or reduction products of the foregoing. The term "phytostanol" as used herein means a hydrogenated form of a phytosterol. Hence, it will be appreciated that hydrogenation modifications, as well as modifications of phytosterol compounds to include, for example, small side chains, are also well within the scope of the present invention.

Any phytosterol or phytostanol which can be incorporated into an edible aqueous mixture and imparts a smooth and pleasing mouth-feel can be utilized in the present invention. In a preferred embodiment, the phytosterol or phytostanol is selected from the group consisting of sitosterol, sitostanol, campesterol, campestanol, taraxasterol, stigmasterol, clionastanol, brassicastanol and brassicasterol, or mixtures thereof. Commercially available phytosterols are often mixtures of phytosterols that are also appropriate for use according to the present invention.

The phytosterols which are used in the present invention can be procured from a variety of natural sources. Phytosterols can be obtained from vegetable oils, vegetable oil sludge, vegetable oil distillates, and other plant oil sources such as tall oils by relatively simple and inexpensive means. For example, a preparation of sterols from vegetable oil sludge by using solvents such as methanol is taught in U.S. Pat. No. 4,420,427. Further, sitosterol can be obtained from cold pressed wheat germ oil, soy extract, or rice extract. (It will be appreciated that natural sitosterol contains about 40% alpha-sitosterol and about 60% beta-sitosterol. Both the alpha and beta forms of sitosterol can be used to form the edible phytosterol compositions of the present invention.) Stigmasterol is also found in trace amounts in cold pressed wheat germ oil, soy extract, saw palmetto and rice extract, and taraxasterol can be obtained from licorice root extract and dandelions.

Although phytostanols are found in small amounts in nature, they can easily be made from the much more abundant phytosterols by hydrogenation. Methods of preparing phytostanols from phytosterols are well-known in the art.

The edible phytosterol/phytostanol composition of the invention also comprises an isolated water soluble protein. As used herein, the term "protein" refers to a molecule comprised of one or more peptides. The term "isolated" means that the material is removed from its original environment (e.g., the natural environment if it is naturally occurring). It is devoid of, in whole or part, components with which the protein is normally associated in nature. For example, a naturally-occurring polypeptide present in a living animal is not isolated, but the same polypeptide, separated from some or all of the coexisting materials in the natural system, is isolated. Such a polypeptide could be part of a composition and still be isolated in that such composition is not part of its natural environment. The term "isolated" does not necessarily denote the method by which the proteins are obtained or the level of purity of the preparations. Thus, an isolated protein of the present invention can be obtained from its natural source, examples of which are disclosed herein. In addition, an isolated protein of the present invention can also be produced using recombinant DNA technology or chemical synthesis.

The protein to be used in preparing the edible composition according to the present invention includes animal and/or plant proteins. In particular, the protein of the present invention can be isolated from any soluble protein source such as milk, whey, wheat, soy or any other vegetable source. Various methods for the isolation of the proteins for use in the invention can be accomplished by procedures well known in the art. In a preferred embodiment, the protein isolates contain from about 30% to about 99% protein on a moisture free basis.

In the present invention, it is preferable to use a water soluble protein. As used herein, the term "water soluble" means water soluble or water dispersible. A water soluble compound can be inherently water soluble or can be made water soluble by the addition of a solubilizing compound, such as a coupling agent, a co-surfactant, or a solvent. Preferably, the isolated water soluble protein has a Nitrogen Solubility Index (NSI) of about 30% to about 95%. Techniques for determining the NSI of a protein are well known in the art.

In a preferred embodiment, the protein source is selected from the group consisting of whey protein, whey protein concentrate, whey powder, soy protein, soy protein isolate, caseinate, (e.g., sodium caseinate, sodium calcium caseinate, calcium caseinate, potassium caseinate), wheat protein, lupin, corn gluten, egg albumen and combinations thereof. More preferably, the protein is soy protein or caseinate. In another preferred embodiment, the weight ratio of the protein to the phytosterol or phytostanol in the edible composition of the invention is from about 1:1 to about 5:1.

In another embodiment of the invention, the phytosterol or phytostanol composition further comprises an emulsifier. By the term "emulsifier" is meant a natural or synthetic substance that promotes the formation and improves the stability of emulsions. The unifying characteristic of emulsifiers is the presence of a hydrophilic group and a lipophilic group on the same molecule. The variability in the performance of different emulsifiers is due to the relative potency of the two kinds of regions, their spatial relationship, the size of the entire molecule and certain other factors. Performance testing is usually the only solution to the problem of selecting an appropriate emulsifier or emulsifier blend.

In a preferred embodiment, the emulsifier used in the invention is a low HLB emulsifier. As used herein, the hydrophilic-lipophilic balance (HLB) of an emulsifier is used to classify the emulsifier in terms of its relative simultaneous attraction to the oil phase and the water phase of an emulsion. See, e.g., Schick, *NonionicSurfactants: Physical Chemistry*, Marcel Dekker, Inc., New York, N.Y., pp. 439–47 (1987). The HLB value of an emulsifier is a term well known to those skilled in the art as are techniques for ascertaining the HLB value.

The HLB value is related to the solubility of the emulsifier, wherein an emulsifier with a low HLB value, e.g., about 10 or less, tends to be oil soluble and an emulsifier with a high HLB value, e.g., greater than about 10, tends to be water soluble. For purposes of this invention, a low HLB emulsifier has an HLB value less than about 10 and a high HLB emulsifier has an HLB greater than about 10. In a preferred embodiment, the emulsifier used in the invention has an HLB value from about 0.1 to about 10. In another preferred embodiment, the low HLB emulsifier is combined with a high HLB emulsifier. For example, polysorbate 60, 65 or 80 can be combined with sodium stearyl lactylate. Preferably, the high HLB emulsifier has a HLB value from about 10 to about 14.

In yet another preferred embodiment of the invention, the emulsifier of the phytosterol/phytostanol composition is selected from the group consisting of lecithin, e.g., deoiled lecithin or modified lecithin, monoglycerides, e.g., distilled monoglycerides or ethoxylated monoglycerides, diglycerides, polyglycerol esters, propylene glycol esters, polysorbates, sodium stearyl lactylate, sucrose esters, maltodextrins and mixtures thereof. More preferably, the emulsifier is lecithin or monoglycerides and diglycerides of fatty acids.

Monoglycerides can be prepared from many types of fats and oils, such as lard and vegetable oils. The monoglycerides suitable for use in accordance with this invention may be prepared, for example, by conventional methods of glycerolysis of edible fats and oils. Distilled monoglycerides may be derived from a variety of sources including, for example, cottonseed oil, corn oil, palm oil, peanut oil, rapeseed oil, soybean oil and canola oil.

Lecithin is a phosphatide found in all living plants and animals. Lecithin is a mixture of the diglycerides of stearic, palmitic, oleic, linoleic and linolenic acids linked to the choline ester of phosphoric acid. Examples of lecithins which may be used include those derived from plants such as soybean, rapeseed, peanut, safflower, cotton seed, sunflower or corn, and those derived from animal sources such as egg yolk.

Lecithin is prepared commercially primarily from soybean oil. It exists preformed in crude soybean oil, and the commercial method of preparation involves precipitation from the oil and subsequent purification. It may be further processed by bleaching, fractionation, hydrolysis, acetylation, extraction, hydroxylation, and the like. In a preferred embodiment, a modified or deoiled lecithin derived from soybean oil is used. Particular reference is made to 21 C.F.R. §184.1400 which describes the use conditions for commercial lecithin.

"Modified" lecithin refers to, but is not limited to, acetylation, hydroxylation, hydrogenation, hydrolysis products of lecithin, chlorination, bromination, iodination, halogenation, phosphorylation and sulfonation. In addition, any other modification known to those in the art is included within the scope of the invention. See, e.g., Szuhaj and List, eds., *Lecithins*, pp. 203–208, American Oil Chemists Society (1985), all of which is incorporated herein by reference.

In many applications, a solid granular or powdered product is desired. Such a product can be made by removing the neutral triglyceride oil from the lecithin. The art separates the oil by extracting with acetone (Szuhaj and List, eds., *Lecithins*, American Oil Chemists Society (1985)), and this is referred to as acetone deoiling.

In another preferred embodiment, the weight ratio of the emulsifier to the phytosterol or phytostanol in the edible composition of the invention is from about 0.2:1 to about 5:1. More preferably, the weight ratio of the emulsifier to the phytosterol or phytostanol is from about 0.5:1 to about 2:1.

In another aspect of the invention there is provided a method of making a non-soluble, water dispersible aqueous edible composition. The method comprises the step of homogenizing an aqueous mixture of an isolated water soluble protein and a phytosterol or phytostanol, wherein the weight ratio of the protein to the phytosterol or phytostanol is from about 0.2:1 to about 10:1, and wherein an aqueous edible composition is produced.

In a preferred embodiment, the method of making the aqueous edible composition comprises the steps of first blending an aqueous mixture of an isolated water soluble protein with a phytosterol or phytostanol, processing the mixture by heating, and then homogenizing the mixture to produce an aqueous edible composition.

The protein to be used in preparing the edible composition according to the present invention includes animal and/or plant proteins. In particular, the protein of the present invention can be isolated from any water soluble protein source such as milk, whey, wheat, soy or any other vegetable source.

In a preferred embodiment, the protein source is selected from the group consisting of whey protein, whey protein concentrate, whey powder, soy protein, soy protein isolate, caseinate, wheat protein, lupin, corn gluten, egg albumen and combinations thereof. More preferably, the protein is soy protein or caseinate. In another preferred embodiment, the weight ratio of the protein to the phytosterol or phytostanol in the edible composition is from about 1:1 to about 5:1.

The phytosterol or phytostanol blended with the aqueous mixture can be any which can be incorporated into an edible aqueous mixture and which imparts a smooth and pleasing mouth-feel. In a preferred embodiment, the phytosterol or phytostanol is selected from the group consisting of sitosterol, sitostanol, campesterol, campestanol, taraxasterol, stigmasterol, clionastanol, brassicastanol and brassicasterol, or mixtures thereof. Commercially available phytosterols are often mixtures of phytosterols that are also appropriate for use according to the present invention.

In a preferred embodiment, the phytosterols or phytostanols are ground or prilled to produce a powdered product before they are added to the aqueous mixture. Prilling is a well known process, and any prilling process known in the art may be used in the present invention. See, e.g., U.S. Pat. No. 4,238,429. Preferably, the phytosterols or phytostanols are spray prilled. Grinding or prilling the phytosterols or phytostanols prior to their addition to the aqueous mixture allows for a free-flowing product, which helps incorporate the compounds into the aqueous system.

In another preferred embodiment, the aqueous mixture further comprises an emulsifier. Preferably, the emulsifier utilized in the edible composition is a low HLB emulsifier that has an HLB value from about 0.1 to about 10. Optionally, the low HLB emulsifier is combined with a high HLB emulsifier having a HLB value from about 10 to about 14.

In another preferred embodiment, the emulsifier is selected from the group consisting of lecithin, e.g., deoiled or modified lecithin, monoglycerides, e.g., distilled or ethoxylated monoglycerides, diglycerides, polyglycerol esters, propylene glycol esters, polysorbates, sodium stearyl lactylate, sucrose esters, maltodextrins and mixtures thereof. More preferably, the emulsifier is lecithin or monoglycerides and diglycerides of fatty acids.

The weight ratio of the emulsifier to the phytosterol or phytostanol can vary from about 0.2:1 to about 5:1. Preferably, the weight ratio of the emulsifier to the phytosterol or phytostanol is from about 0.5:1 to about 2:1.

The aqueous mixture comprising an isolated water soluble protein, a phytosterol or phytostanol and optionally an emulsifier is then heated to an appropriate temperature. In a preferred embodiment, the aqueous mixture is heated to a temperature of about 60° C. to about 145° C. More preferably, the mixture is heated to a temperature of about 80° C. to about 100° C.

The homogenizing step may be accomplished with any conventional homogenizing equipment with either a single stage or a two-stage operation. The aqueous mixture is homogenized at a pressure which allows the integration of the phytosterols or phytostanols with the protein and the emulsifier. Preferably, the aqueous mixture is homogenized at a pressure between 1,000 and 10,000 pounds per square inch. More preferably, the mixture is homogenized at a pressure between 2,000 and 5,000 pounds per square inch.

The aqueous edible phytosterol or phytostanol composition may be used as an ingredient in the manufacture of another food product, as an additive in food products or alone as a functional food. For example, the aqueous edible composition may be used as an ingredient in a beverage, frozen desert, baked good, meat product or any other food product where a liquid ingredient can be used. The composition has a smooth mouth-feel which does not impart any graininess.

In another embodiment of the invention, the aqueous phytosterol or phytostanol composition is dried after homogenization to produce a water dispersible powder. The process used for drying the aqueous mixture is not critical. Any process known in the art which would produce a good free-flowing dispersible product may be used. For example, the aqueous mixture can be spray-dried, flash-dried, freeze-dried or dried in any other way which produces a powder either directly or through a grinding step.

The dried powder can then be used as an ingredient in a finished food product which requires powder as an ingredient, as a food additive or alone as a functional food. Further, the powder is storage stable. The co-dried phytosterol/phytostanol-protein powder of the invention allows high melting hydrophobic phytosterols and phytostanols to be incorporated into aqueous products such as, e.g., nutritional beverages or powdered mixes.

In another aspect of the present invention there is provided an edible phytosterol or phytostanol composition which is produced by any one of the above methods.

In another aspect of the invention there is provided a method of producing an edible product. The method comprises blending a first ingredient comprising one or more edible compounds in an appropriate form with a second ingredient comprising the edible phytosterol or phytostanol composition of the present invention to produce a mixture, and then processing the mixture to produce an edible product. In one embodiment, the edible product is a solid edible product. In another embodiment, the edible product is a beverage. It is also to be understood that the edible phytosterol or phytostanol composition can be added before, during or after the production of the edible product.

In yet another aspect of the present invention there is provided an edible product which comprises the phytosterol or phytostanol composition of the invention. There are no restrictions to the foods and beverages which may contain the edible composition of the present invention. The edible product need not contain cholesterol or triglycerides, and the product may be either in solid or liquid form. Due to the unique methods and compositions of the invention, the phytosterols or phytostanols will remain dispersed in the edible product. In a further aspect of the invention there is provided a non-soluble, water-dispersible aqueous edible composition comprising a compound selected from the group consisting of phytosterols and phytostanols and a maltodextrin, wherein the weight ratio of the maltodextrin to the compound is from about 0.2:1 to about 10:1.

All patents and publications cited in this disclosure are indicative of the level of skill of those skilled in the art to which this invention pertains and are all herein incorporated by reference in their entirety.

Having now generally described the invention, the same will be more readily understood through reference to the following Examples which are provided by way of illustration, and are not intended to be limiting of the present invention, unless specified.

EXAMPLE 1

Preparation of a Phtytosterol Composition

A phytosterol composition was prepared using the following method. 1056 grams of soy protein isolate was added to 8444 grams of 120° F. water under good agitation and then hydrated for 15 minutes. 200 grams of phytosterols and 300 grams of deoiled lecithin was added, and the liquid mixture was agitated for 5 minutes. The mixture was then added to a Groen kettle (Groen Manufacturing Co., Jackson, Miss.) and heated to a temperature of 185° F. for 10 minutes. The liquid mixture was then homogenized at 3500/500 psi and spray dried with a 480° F. inlet and a 180° F. outlet temperature.

EXAMPLE 2

Preparation of a Phytosterol Composition Using Caseinate

A phytosterol composition using caseinate as the isolated protein was prepared using the following method. 1056 grams of sodium caseinate was added to 8444 grams of 120° F. water under good agitation and then hydrated for 15 minutes. 200 grams of phytosterols and 300 grams of deoiled lecithin was added, and the liquid mixture was agitated for 5 minutes. The mixture was then added to a Groen kettle (Groen Manufacturing Co., Jackson, Miss.) and heated to a temperature of 185° F. for 10 minutes. The liquid mixture was then homogenized at 3500/500 psi and spray dried with a 480° F. inlet and a 180° F. outlet temperature.

EXAMPLE 3

Preparation of a Phytosterol Composition Using Mono- and Diglycerides

A phytosterol composition using monoglycerides and diglycerides as the emulsifier was prepared using the following method. 1056 grams of soy protein isolate was added to 8444 grams of 120° F. water under good agitation and then hydrated for 15 minutes. 200 grams of phytosterols and 300 grams of mono- and diglycerides was added, and the liquid mixture was agitated for 5 minutes. The mixture was then added to a Groen kettle (Groen Manufacturing Co., Jackson, Miss.) and heated to a temperature of 185° F. for 10 minutes. The liquid mixture was then homogenized at 3500/500 psi and spray dried with a 480° F. inlet and a 180° F. outlet temperature.

EXAMPLE 4

Preparation of a Phytosterol Composition With a Low Protein Content

A phytosterol composition with a lower protein content was prepared using the following method. 150 grams of soy protein isolate was added to 9350 grams of 120° F. water under good agitation and then hydrated for 15 minutes. 200 grams of phytosterols and 300 grams of deoiled lecithin was added, and the liquid mixture was agitated for 5 minutes. The mixture was then added to a Groen kettle (Groen Manufacturing Co., Jackson, Miss.) and heated to a temperature of 185° F. for 10 minutes. The liquid mixture was then homogenized at 3500/500 psi and spray dried with a 480° F. inlet and a 180° F. outlet temperature.

EXAMPLE 5

Preparation of a Phytosterol Composition With a Low Emulsifier Content

A phytosterol composition was prepared with a lower emulsifier content using the following method. 1056 grams of soy protein isolate was added to 8644 grams of 120° F.

water under good agitation and then hydrated for 15 minutes. 200 grams of phytosterol and 100 grams of deoiled lecithin was added, and the liquid mixture was agitated for 5 minutes. The mixture was then added to a Groen kettle (Groen Manufacturing Co., Jackson, Miss.) and heated to a temperature of 185° F. for 10 minutes. The liquid mixture was then homogenized at 3500/500 psi and spray dried with a 480° F. inlet and a 180° F. outlet temperature.

In view of the foregoing description taken with the Examples, it is understood that certain modifications should be and will be apparent to those of ordinary skill in the art, and that such modifications to the precise methods and compositions as set forth herein are intended to come within the spirit and scope of the invention as defined in the appended claims either literally or by the doctrine of equivalents.

What is claimed is:

1. An edible composition comprising:
   (a) a compound selected from the group consisting of phytosterols and phytostanols;
   (b) an isolated water soluble or water dispersible protein selected from the group consisting of whey protein, soy protein, wheat protein, lupin, corn gluten and caseinate; and
   (c) lecithin;
   wherein the weight ratio of said protein (b) to said compound (a) is from about 0.2:1 to about 10:1, wherein the weight ratio of said lecithin (c) to said compound (a) is from about 0.5:1 to about 2:1, wherein said lecithin has a hydrophilic-lipophiilic balance value from about 0.1 to about 10, wherein said composition does not contain oil as a solubilizing agent, and wherein said composition is dried to a water dispersible powder.

2. The composition of claim 1, wherein said compound (a) is selected from the group consisting of sitosterol, sitostanol, campesterol, campestanol, taraxasterol, stigmasterol, clionastanol, brassicastanol and brassicasterol, or mixtures thereof.

3. The composition of claim 1, wherein said composition lowers serum cholesterol in animals or humans.

4. The composition of claim 1, wherein said protein (b) is soy protein.

5. The composition of claim 1, wherein said lecithin is deoiled lecithin.

6. The composition of claim 1, further comprising choline.

7. An edible product comprising the composition of claim 1.

8. The product of claim 7, wherein said product is a solid edible product.

9. The product of claim 7, wherein said product is a beverage.

10. An edible composition comprising:
    (a) a phytostanol;
    (b) an isolated water soluble or water dispersible protein selected from the group consisting of whey protein, soy protein, wheat protein, lupin, corn gluten and caseinate; and
    (c) lecithin;
    wherein the weight ratio of said protein (b) to said phytostanol (a) is from about 0.2:1 to about 10:1, wherein said lecithin has a hydrophilic-lipophilic balance value from about 0.1 to about 10, wherein said composition does not contain oil as a solubilizing agent, and wherein said composition is dried to a water dispersible powder.

11. The composition of claim 10, wherein said phytostanol (a) is selected from the group consisting of sitostanol, campestanol, clionastanol and brassicastanol, or mixtures thereof.

12. The composition of claim 10, wherein said protein (b) is soy protein.

13. The composition of claim 10, wherein said lecithin is deoiled lecithin.

14. The composition of claim 10, further comprising choline.

15. The composition of claim 10, wherein the weight ratio of said lecithin to said phytostanol (a) is from about 0.5:1 to about 2:1.

16. The composition of claim 10, wherein said composition lowers serum cholesterol in animals or humans.

17. An edible product comprising the composition of claim 10.

18. The product of claim 17, wherein said product is a solid edible product.

19. The product of claim 17, wherein said product is a beverage.

\* \* \* \* \*

UNITED STATES PATENT AND TRADEMARK OFFICE
CERTIFICATE OF CORRECTION

PATENT NO. : 6,677,327 B1 Page 1 of 1
DATED : January 13, 2004
INVENTOR(S) : Gottemoller It is certified that error appears in the above-identified patent and that said Letters Patent is hereby corrected as shown below:

Title page,
Item [56], References Cited, FOREIGN PATENT DOCUMENTS, under "WO 99/39715", please delete "9/1999" and insert -- 8/1999 -- therefor.

Column 1,
Line 49, please delete the word "oilsolubilized" and insert -- oil-solubilized -- therefor.

Signed and Sealed this

Fifteenth Day of June, 2004

JON W. DUDAS
*Acting Director of the United States Patent and Trademark Office*